United States Patent
Tao

(10) Patent No.: US 8,853,389 B2
(45) Date of Patent: Oct. 7, 2014

(54) PROCESS FOR REFINING CEFMETAZOLE SODIUM

(75) Inventor: Linggang Tao, Wuyi (CN)

(73) Assignee: Hainan Lingkang Pharmaceutical Co., Ltd., Hainan (CN)

( * ) Notice: Subject to any disclaimer, the term of this patent is extended or adjusted under 35 U.S.C. 154(b) by 0 days.

(21) Appl. No.: 13/997,613

(22) PCT Filed: Apr. 14, 2011

(86) PCT No.: PCT/CN2011/000659
§ 371 (c)(1),
(2), (4) Date: Jun. 24, 2013

(87) PCT Pub. No.: WO2012/126147
PCT Pub. Date: Sep. 27, 2012

(65) Prior Publication Data
US 2014/0005381 A1    Jan. 2, 2014

(30) Foreign Application Priority Data

Mar. 24, 2011 (CN) .......................... 2011 1 0072690

(51) Int. Cl.
*C07D 501/12* (2006.01)
*C07B 63/00* (2006.01)

(52) U.S. Cl.
CPC .............. *C07D 501/12* (2013.01); *C07B 63/00* (2013.01)
USPC ........................................ 540/220

(58) Field of Classification Search
USPC ........................................... 540/220
See application file for complete search history.

(56) References Cited

FOREIGN PATENT DOCUMENTS

| CN | 101550151 A | 10/2009 | |
| CN | 101787039 A * | 7/2010 | ........... C07D 501/57 |
| CN | 101787039 A | 7/2010 | |

* cited by examiner

*Primary Examiner* — Golam M M Shameem
*Assistant Examiner* — Laura Daniel
(74) *Attorney, Agent, or Firm* — CBM Patent Consulting, LLC

(57) ABSTRACT

The present invention relates to a novel process for refining Cefmetazole sodium, comprising the steps of: 1) dissolving Cefmetazole sodium material in water, and extracting after adding a water-immiscible organic solvent(s), followed by separating the organic phase containing impurities, to provide an aqueous phase containing Cefmetazole sodium; 2) treating by adding an alkoxide of alkali metal or alkaline earth metal into the above aqueous phase, followed by filtrating the precipitate, to provide an aqueous filtrate; and 3) adding ethanol or acetone in the aqueous solution and recrystallizing, followed by centrifuging and washing the resultant crystals, to provide the refined and purified Cefmetazole sodium after drying. The purity of Cefmetazole sodium material can be greatly improved by the process of the present invention.

14 Claims, 1 Drawing Sheet

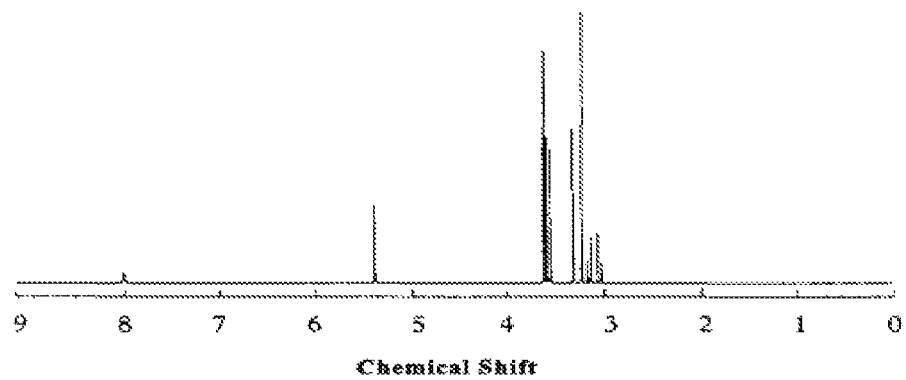

PROCESS FOR REFINING CEFMETAZOLE SODIUM

FIELD OF THE INVENTION

The present invention relates to a novel process for refining Cefmetazole sodium, and belongs to the medical technical filed.

BACKGROUND ART

Cefmetazole sodium has the chemical name (6R,7S)-3-{[(1-methyl-1H-tetrazol-5-yl)thio]methyl}-7-[2-(thiocyanomethyl)acetamido]-7-methoxy-S-oxo-5-thia-1-azabicyclo[4.2.0]oct-2-ene-2-formic acid sodium salt and a molecular formula of $C_{15}H_{16}N_7NaO_5S_3$ with a molecular weight of 493.52. The content of Cefmetazole sodium is not less than 86.0%, calculated on the anhydrous. The structure of Cefmetazole sodium is as follows:

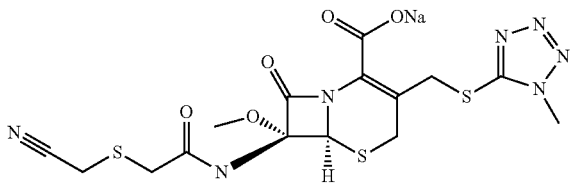

Cefmetazole sodium is a second generation cephalosporin, and is more stable towards broad-spectrum β-lactamase generated by negative bacilli. It shows relatively good activity against negative bacilli such as Escherichia coli, Klebsiella pneumoniae, Proteus mirabilis, Shigella, Salmonella, etc., high sensitivity to Staphylococcus aureus, group A hemolytic streptococcus and catarrhal Brenham bacteria, good antibacterial activity against Bacteroides fragilis, and low sensitivity or resistance to Enterobacter, Pseudomonas, methicillin-resistant Staphylococcus aureus, pneumococcus, and meningococcus. It is clinically useful for the treatment of various infections induced by sensitive bacteria, such as respiratory infections, biliary tract infections, urinary tract infections, obstetrics and gynecology bacterial infections, skin and soft tissue infections, and prevention of post-operative infections.

A number of domestic and foreign references of patents and journals have disclosed processes for preparing and refining Cefmetazole sodium.

Chinese Patent CN101550151A discloses a process for preparing Cefmetazole sodium, wherein 7β-amino-7α-methoxy-3-(1-methyl-1H-tetrazol-5-thiomethyl)-3-cephem-4-carboxylic acid benzyl ester is mixed and reacted with sodium cyanomethylthioacetate in the presence of p-toluenesulfonyl chloride, generating Cefmetazole, which is treated with added sodium hydroxide to form Cefmetazole sodium. However, the yield and the purity of Cefmetazole sodium prepared by this method are low.

Chinese Patent CN101787039A reports a process for preparing and refining Cefmetazole sodium. Although the purity of Cefmetazole sodium is improved, the inherent impurities in the drug substance is difficult to separate by simple reconciling with acids and bases, and additional negative ion impurities may be introduced in the pH adjusting process, thereby increasing the difficulties in separation.

Currently, Cefmetazole sodium is manufactured mainly dependent on dispensing from imported raw material drugs by domestic pharmaceutical manufacturers. Although Cefmetazole sodium is produced in China, however, both the yield and the product purity are still low. Therefore, how to improve the purity of Cefmetazole sodium is a pending problem anxiously to be solved, which possesses significant social and economic benefits.

DETAILED DESCRIPTION OF THE INVENTION

The present invention provides a process for refining Cefmetazole sodium compound, in order to overcome the above defects existing in the prior art, especially the low purity of Cefmetazole sodium prepared by the prior art.

The Cefmetazole sodium used in the present refining process can be Cefmetazole sodium crude material obtained from any known process in the prior art for preparing Cefmetazole sodium or any commercially available or imported Cefmetazole sodium drug substance, hereinafter generally referred to as Cefmetazole sodium material used according to the present invention.

After intensive studies, the inventors found that the purity of Cefmetazole sodium material can be substantially improved by a refining process which comprises the steps of:

1) dissolving Cefmetazole sodium material in water, and extracting after adding a water-immiscible organic solvent(s), preferably ethyl acetate, cyclohexane, or a mixture of ethyl acetate and cyclohexane, followed by separating the organic phase containing impurities, to provide a primarily purified Cefmetazole sodium in the aqueous phase;

2) treating by adding an alkoxide of alkali metal or alkaline earth metal into the above aqueous phase, optionally under heating during the treating process, followed by cooling down and filtrating the precipitate to provide a filtrate, which is a secondarily purified Cefmetazole sodium aqueous solution; and 3) adding in the aqueous solution a poor solvent of Cefmetazole sodium, preferably ethanol or acetone, and recrystallizing under controlled temperature, followed by centrifuging and washing the resultant crystals, to provide a thirdly purified Cefmetazole sodium after drying.

The present invention is further illustrated as follows.

Step 1)

The Cefmetazole sodium material is dissolved in water, and the solution is extracted after adding a water-immiscible organic solvent or a mixture of solvents, followed by separating the organic phase, to provide an aqueous solution containing Cefmetazole sodium;

The organic solvent is preferably ethyl acetate, cyclohexane, or a mixture of ethyl acetate and cyclohexane, more preferably ethyl acetate.

The volume of the organic solvent is preferably less than half of the volume of the aqueous solution, more preferably less than one third of the volume of the aqueous solution. Multiple extractions can be carried out, preferably 2-3 times. In order to make thorough extraction, stirring is preferably applied, followed by removing the organic phase containing impurities by dispensing.

Extractions are conducted based on the following reason: under normal circumstances, the Cefmetazole sodium material contains solvents introduced during preparation, various raw materials and intermediate products, moisture introduced by hygroscopicity, bacterial endotoxin, and various inorganic compounds and heavy metals, etc. These substances exist as impurities, affecting the purity of the Cefmetazole sodium material. Although the content of these substances is very low, they are still dissolved in the Cefmetazole sodium aqueous solution in minor or trace amounts. We note that some of these impurity-like substances show high solubility in an organic solvent, and extraction is a common and effective separating method.

Step 2)

The above aqueous phase is treated by adding an alkoxide of alkali metal or alkaline earth metal, and heating optionally during the treating process, followed by cooling down and filtrating the precipitate, to provide the filtrate as an aqueous solution containing Cefmetazole sodium.

In principle, any alkoxide (i.e. alcoholate) of alkali metal or alkaline earth metal can be used, preferably an alkoxide of alkali metal, more preferably an alkoxide of sodium or potassium, such as sodium methoxide, sodium ethoxide, potassium methoxide, or potassium ethoxide.

The alkoxide of alkali metal or alkaline earth metal is normally first dissolved in water or an alcohol solvent, preferably in water, or dissolved in a solvent with the same anion, for example, sodium methoxide or potassium methoxide is dissolved in methanol, and sodium ethoxide or potassium ethoxide is dissolved in ethanol.

The temperature for treating Cefmetazole sodium with the alkoxide of alkali metal or alkaline earth metal is in the range of 30-100° C., preferably in the range of 40-80° C. In order to fully hydrolyze, it is more preferably in the range of 50-70° C.

The treating time is normally from several minutes to several hours, preferably from 30 minutes to 5 hours, more preferably 1-3 hours, most preferably 2 hours.

After the above treatment, a small amount of precipitation is formed. The amount of precipitation increases with decreasing temperature.

Without being bound by any principle, the purification effect by treatment with the alkoxide of alkali metal or alkaline earth metal in step 2) of the present invention is based on the following reason: the last step for many Cefmetazole sodium preparation methods is to remove the carboxyl protecting group, followed by forming a sodium salt from the carboxyl group. For example, the ester group is a common protecting group for the carboxyl group, which will inevitably lead to the existence of a small amount of ester impurities in the crude products of Cefmetazole sodium. In the presence of alkaline substances such as an alkoxide of alkali metal or alkaline earth metal, it is beneficial for the residual esters to be hydrolyzed into Cefmetazole sodium, not only effectively reducing the impurities but also advantageously improving the yield of the target product. Meanwhile, some impurity substances are soluble in the solution of the alkoxide of alkali metal or alkaline earth metal, especially when an alcohol is used as the solvent to dissolve the alkoxide of alkali metal or alkaline earth metal, thus the separation of these impurity substances and Cefmetazole sodium is realized.

Step 3)

A poor solvent of Cefmetazole sodium is added in the aqueous solution, preferably ethanol or acetone, and recrystallized under controlled temperature, followed by centrifuging and washing the resultant crystals, to provide thirdly purified Cefmetazole sodium after drying.

We find that by using the commonly used methods of recrystallization in refluxing solvent or suspension in a solvent(s) under stirring and refluxing conditions for Cefmetazole sodium, it is either hard to crystalize or impurities are wrapped in the precipitation. Direct use of the precipitation method in a benign-poor solvent(s) for the Cefmetazole sodium crude material cannot achieve the desired purity either.

Since the solubility of Cefmetazole sodium is high in water but very low in ethanol and even lower in acetone, a mixture of water and ethanol or a mixture of water and acetone is chosen as the solvent to recrystallize Cefmetazole sodium.

Surprisingly, after treatments in steps 1) and 2) of the present invention, crystals with very high purity are acquired by recrystallization in the mixture of water and ethanol or in the mixture of water and acetone in appropriate proportions as the solvent to dissolve Cefmetazole sodium. The reason might be the impurity substances that have an adverse effect on recrystallization are already removed in steps 1) and 2) of the present invention, and it is more suitable for the Cefmetazole sodium product treated by the alkoxide alkali metal or alkaline earth metal to recrystallize in these mixture solvents.

During recrystallization, first at elevated temperature such as at 30-80° C., the provided Cefmetazole sodium aqueous solution in step 2) is concentrated to reduce the water content, followed by adding ethanol with a water-ethanol volume ratio of 4:6 or adding acetone with a water-acetone volume ratio of 5:5. Under slowly cooling-down conditions until the temperature reaches between room temperature and −5° C., crystals are precipitated slowly during this process, and the Cefmetazole sodium seed crystals are introduced optionally during the cooling process. Crystallization is completed after being placed for 5-48 hours and the crystals can be dried by air or in vacuum.

BRIEF DESCRIPTION OF THE DRAWINGS

FIG. 1 is the $^1$H NMR spectrum of Cefmetazole sodium prepared in the example.

EMBODIMENTS OF THE INVENTION

The present invention provides a process for refining Cefmetazole sodium, characterized in comprising the steps of:

1) dissolving Cefmetazole sodium material in water, adding ethyl acetate, cyclohexane, or a mixture of ethyl acetate and cyclohexane, and extracting for several times with the volume of the organic solvent preferably less than half of the volume of the aqueous solution each time, followed by separating the organic phase, to provide an aqueous phase containing Cefmetazole sodium;

2) treating by adding an alkoxide of alkali metal or alkaline earth metal into the above aqueous phase under heating, preferably at a temperature of 30-100° C., for a time range from several minutes to several hours, preferably from 30 minutes to 5 hours, followed by cooling down and filtrating the precipitate, to provide an aqueous filtrate; and 3) concentrating the Cefmetazole sodium aqueous solution provided in step 2) at elevated temperature, such as at 30-80° C., and recrystallizing by adding ethanol with a water-ethanol volume ratio of 4:6 or adding acetone with a water-acetone volume ratio of 5:5 under slowly cooling-down conditions until the temperature reaches between room temperature and −5° C., followed by centrifuging and washing the resultant crystals, to provide a thirdly purified Cefmetazole sodium after drying.

In an embodiment of the present invention, the organic solvent in step 1) is ethyl acetate.

In an embodiment of the present invention, the volume of the organic solvent in step 1) is less than one third of the volume of the aqueous solution in each extraction and the number of extractions is 2-3.

In an embodiment of the present invention, the treating temperature in step 2) is 40-80° C., preferably 50-70° C., and the treating time is 1-3 hours, preferably 2 hours.

In an embodiment of the present invention, in step 3) ethanol is used to wash the crystals if recrystallizing by adding ethanol with a water-ethanol volume ratio of 4:6, and acetone is used to wash the crystals if recrystallizing by adding acetone with a water-acetone volume ratio of 5:5.

In an embodiment of the present invention, the temperature after adding the solvent in step 3) is cooled down to between room temperature and −5° C., and the Cefmetazole sodium seed crystals are introduced optionally during the cooling process.

In an embodiment of the present invention, crystallization is completed after being placed for 5-48 hours in step 3) and the crystals can be dried by air or in vacuum.

The refined Cefmetazole sodium obtained from the above embodiments shows that the content of Cefmetazole is not less than 94%, mostly not less than 94.5%, according to the high-performance liquid chromatography (Chinese Pharmacopoeia 2000 Edition part two Appendix VD), and the color is white.

Since the powder flowability, specific dissolution rate, solid stability of Cefmetazole sodium and the operability of the process play important roles in the activity of Cefmetazole sodium and the preparations thereof, Cefmetazole sodium with substantially increased purity brings about a significant improvement in the dissolution rate, the formulatability and the stability.

Therefore, the Cefmetazole sodium refined according to the process of the present invention is highly suitable to be formulated an antimicrobial pharmaceutical composition for the treatment of various infections induced by sensitive bacteria, such as respiratory infections, biliary tract infections, urinary tract infections, obstetrics and gynecology bacterial infections, skin and soft tissue infections, and prevention of post-operative infections, wherein the pharmaceutical composition comprises the Cefmetazole sodium refined according to the process of the present invention and pharmaceutically acceptable excipients. Preferably, the pharmaceutical composition can be a lyophilized powder ampul, or a formulation for injection.

The present invention also provides use of the above pharmaceutical composition in the preparation of an antimicrobial medicine for the treatment of various infections induced by sensitive bacteria, such as respiratory infections, biliary tract infections, urinary tract infections, obstetrics and gynecology bacterial infections, skin and soft tissue infections, and prevention of post-operative infections.

The present invention has fundamentally changed the current situation of low purity of the Cefmetazole sodium material, solved the problem existing in Cefmetazole sodium crude material and Cefmetazole sodium drug substances, and reduced a series of clinical adverse reactions due to the presence of excessive insoluble particles or polymer impurities. The present invention also has advantages of convenience, easy to control and industrialization.

The following examples are intended to further explain or illustrate the present invention, and the examples provided should not be understood as limiting the protective scope of the present invention.

The Purity Measurement of Cefmetazole Sodium by HPLC

Instruments and Reagents: Agilent 1100 type high performance liquid chromatography (HPLC). The water is double-distilled water and the acetonitrile is chromatographic grade. Cefmetazole sodium control (National Institute for the Control of Pharmaceutical and Biological Products); Cefmetazole sodium powder ampul for injection (Harbin Pharmaceutical Group Pharmaceutical Factory, specifications 0.5 g); Cefmetazole sodium sample refined according to the process of the present invention.

Chromatographic Conditions: Octadecylsilane-bonded silica as fillers; a buffer containing ammonium dihydrogen phosphate (pH3.5, adjusted by 10% dilute phosphoric acid)—acetonitrile (83:17) as mobile phase with a detection wavelength at 272 nm. The theoretical plates calculated according to Cefmetazole sodium peak should be no less than 2500.

Detailed Procedures: 25 mg of Cefmetazole sodium sample is placed into a 50 mL volume flask. The mobile phase is added into the flask to dissolve the sample and the solution is diluted until liquid surface reaches the mark on the volume flask. After shaking, 10 μL of the solution is injected into the liquid chromatograph and the chromatogram is recorded. Another proper amount of Cefmetazole control sample is determined using the same method. The content of Cefmetazole in samples can be calculated by external standard method. Based on anhydrous material, the content of Cefmetazole should be no less than 86.0%, with a maximum Cefmetazole content of 95.34%.

Example 1

10 g of Cefmetazole sodium crude material, prepared according to CN 101550151 A, is determined to have Cefmetazole content of 83% by High Performance Liquid Chromatography. The crude Cefmetazole sodium is dissolved in 200 mL water, and then the solution is extracted twice by addition of ethyl acetate with 40% volume of the aqueous solution each time. After sufficient stirring and settling, the organic phase is separated out to obtain the aqueous phase containing Cefmetazole sodium.

The above mentioned aqueous phase is treated with 20 mL of 1M sodium ethoxide aqueous solution, under the treatment temperature of 60° C. for 3 hours. Then the solution is cooled to room temperature and precipitation is formed. The aqueous filtrate is obtained after filtration.

The Cefmetazole sodium aqueous solution obtained above is concentrated by warming up to 70° C., until the solution volume is 120 mL. Then, ethanol with an ethanol/water volume ratio of 4:6 is added to the aqueous solution. The solution is slowly cooled down to 15° C. to recrystallize and form crystals. The solution is allowed to stand for 10 hours until no more crystals are formed. After centrifugation in a centrifuge and filteration, the obtained filter cake is washed with analytically pure ethanol and air-dried to give 9.6 g of Cefmetazole sodium, with a yield of 96%.

The $^1$H-NMR spectrum of the purified Cefmetazole sodium prepared according to the present invention is shown in FIG. 1. $^1$H-NMR: δ (1H)=5.4, s; δ (2H)=3.06, s; δ (2H)=3.60, s; δ (3H)=3.63, d; δ (3H)=3.24, s; δ (2H)=3.56, s; δ (2H)=3.33, s; δ (1H)=8.0, s.

The Cefmetazole content is measured as 94.3% by High Performance Liquid Chromatography (HPLC). A sample of the refined material is made into a solution of about 0.1 g/mL by adding water, and the solution is clear and colorless.

Comparative Example 1

The crude Cefmetazole sodium sample applied in Example 1 is purified using the purification method described in Chinese patent CN 101787039 A. The Cefmetazole content is measured as 87% by High Performance Liquid Chromatography (HPLC).

Example 2

10 g of Cefmetazole sodium raw material drugs (Harbin Pharmaceutical Group Pharmaceutical Factory, Batch number 20100601) with 89% Cefmetazole content as determined by High Performance Liquid Chromatography (HPLC), is dissolved in 150 mL water. The aqueous solution is extracted three times by addition of cyclohexane with 35% volume of the aqueous solution each time. Every time the solution is sufficiently stirred and settled, and then the organic phase is separated out to obtain the aqueous phase containing Cefmetazole sodium.

The above mentioned aqueous phase is treated with 15 mL of 2M sodium ethoxide solution in ethanol, under the treatment temperature of 50° C. for 5 hours. Then the solution is cooled to room temperature and precipitation is formed. The aqueous/ethanol filtrate containing Cefmetazole sodium is obtained after filtration.

The Cefmetazole sodium solution obtained above is concentrated by warming up to 65° C., until the solution volume is 100 mL. Then, ethanol with an ethanol/solution volume ratio of 4:6 is added to the solution. The solution is slowly cooled down to 10° C. to recrystallize and form crystals. The solution is allowed to stand for 15 hours until no more crystals are formed. After centrifugation in a centrifuge and filteration, the obtained filter cake is washed with analytically pure ethanol and air-dried to give 9.7 g of Cefmetazole sodium, with a yield of 97%.

The Cefmetazole content is measured as 95.1% by High Performance Liquid Chromatography (HPLC). A sample of the refined material is made into a solution of about 0.1 g/mL by adding water, and the solution is clear and colorless.

Example 3

10 g of Cefmetazole sodium raw material drugs with early manufacturing date (Chongqing Yaoyou Pharmaceutical Co. Ltd., Batch number 20060303), is determined to have Cefmetazole content of 84% by High Performance Liquid Chromatography (HPLC). The crude Cefmetazole sodium is dissolved in 250 mL water. The aqueous solution is extracted three times by addition of a mixture of cyclohexane and ethyl acetate (1:1) with 30% volume of the aqueous solution each time. The solution is sufficiently stirred and settled, and then the organic phase is separated out to obtain the aqueous phase containing Cefmetazole sodium.

The above mentioned aqueous phase is treated with 25 mL of 1M sodium methoxide aqueous solution, under the treatment temperature of 55° C. for 4 hours. Then the solution is cooled to room temperature and precipitation is formed. The aqueous filtrate is obtained after filtration.

The Cefmetazole sodium solution obtained above is concentrated by warming up to 75° C., until the solution volume is 180 mL. Then, acetone with an acetone/water volume ratio of 5:5 is added to the solution. The solution is slowly cooled down to 12° C. to recrystallize and form crystals. The solution is allowed to stand for 12 hours until no more crystals are formed. After centrifugation in a centrifuge and filteration, the obtained filter cake is washed with acetone and dried in vacuum to give 9.5 g of white Cefmetazole sodium, with a yield of 95%.

The Cefmetazole content is measured as 94.6% by High Performance Liquid Chromatography (HPLC). A sample of the refined material is made into a solution of about 0.1 g/mL by adding water, and the solution is clear and colorless.

Example 4

10 g of expired Cefmetazole sodium raw material drugs is determined to have Cefmetazole content of 79% by High Performance Liquid Chromatography (HPLC). The crude Cefmetazole sodium is dissolved in 300 mL water. The aqueous solution is extracted four times by addition of a mixture of cyclohexane and ethyl acetate (2:3) with 25% volume of the aqueous solution each time. Every time the solution is sufficiently stirred and settled, and then the organic phase is separated out to obtain the aqueous phase containing Cefmetazole sodium.

The above mentioned aqueous phase is treated with 20 mL of 1.5M sodium methoxide aqueous solution, under the treatment temperature of 65° C. for 3 hours. Then the solution is cooled to room temperature and precipitation is formed. The aqueous filtrate is obtained after filtration.

The Cefmetazole sodium solution obtained above is concentrated by warming up to 80° C., until the solution volume is 200 mL. Then, acetone with an acetone/water volume ratio of 5:5 is added to the solution. The solution is slowly cooled down to 8° C. to recrystallize and form crystals. The solution is allowed to stand for 9 hours until no more crystals are formed. After centrifugation in a centrifuge and filteration, the obtained filter cake is washed with acetone and dried in vacuum to give 9.55 g of white Cefmetazole sodium, with a yield of 95.5%.

The Cefmetazole content is measured as 94.4% by High Performance Liquid Chromatography (HPLC). A sample of the refined material is made into a solution of about 0.1 g/mL by adding water, and the solution is clear and colorless.

The present invention has been already illustrated according to the above examples. The foregoing examples are only intended to exemplify the present invention. It will be appreciated that numerous modifications and embodiments may be devised by the skilled in the art without deviating the spirit and essence of the present invention. Such modifications are also understood to fall within the protective scope of the present invention.

The invention claimed is:

1. A process for refining Cefmetazole sodium, characterized in that, it comprises the steps of:
    1) dissolving Cefmetazole sodium-contained raw material in water, and extracting after adding a water-immiscible organic solvent(s) selecting from a group consisting of ethyl acetate, cyclohexane, and a mixture of ethyl acetate and cyclohexane, followed by separating the organic phase containing impurities, to provide a primarily purified Cefmetazole sodium in the aqueous phase;
    2) treating by adding an alkoxide of alkali metal or alkaline earth metal into the above aqueous phase, optionally under heating during the treating process, followed by cooling down and filtrating the precipitate to provide a filtrate, which is a secondarily purified Cefmetazole sodium aqueous solution; and
    3) adding in the aqueous solution a solvent selecting from a group consisting of ethanol, acetone and a mixture of ethanol and acetone, and recrystallizing by decreasing the temperature until it reaches between room temperature and −5° C., followed by centrifuging and washing the resultant crystals, to provide a thirdly purified Cefmetazole sodium after drying.

2. The process for refining Cefmetazole sodium according to claim 1, characterized in that, the organic solvent in step 1) is ethyl acetate.

3. The process for refining Cefmetazole sodium according to claim 1, characterized in that, the volume of the organic solvent in step 1) is less than one third of the volume of the aqueous solution in each extraction and the number of extractions is 2 or 3.

4. The process for refining Cefmetazole sodium according to claim 1, characterized in that, the treating temperature in step 2) is 40-80° C., and the treating time is 1-3 hours, preferably 2 hours.

5. The process for refining Cefmetazole sodium according to claim 1, characterized in that, in step 3) ethanol is used to wash the crystals if recrystallizing by adding ethanol with a water-ethanol volume ratio of 4:6, and acetone is used to wash the crystals if recrystallizing by adding acetone with a water-acetone volume ratio of 5:5.

6. The process for refining Cefmetazole sodium according to claim 1, characterized in that, the temperature after adding the solvent in step 3) is cooled down to between room temperature and −5° C., and Cefmetazole sodium seed crystals are introduced optionally during the cooling process.

7. The process for refining Cefmetazole sodium according to claim 1, characterized in that, crystallization is completed between 5 and 48 hours in step 3) and the crystals can be dried by air or in vacuum.

8. A process for refining Cefmetazole sodium, characterized in that, the process comprises the steps of:
1) dissolving Cefmetazole sodium-contained raw material in water, adding ethyl acetate, cyclohexane, or a mixture of ethyl acetate and cyclohexane, and extracting for several times with the volume of the organic solvent less than half of the volume of the aqueous solution each time, followed by separating the organic phase, to provide an aqueous phase containing Cefmetazole sodium;
2) treating by adding an alkoxide of alkali metal or alkaline earth metal into the above aqueous phase at a temperature of 30-100° C., for a time range from 30 minutes to 5 hours, followed by cooling down and filtrating the precipitate, to provide an aqueous filtrate; and
3) concentrating the Cefmetazole sodium aqueous solution provided in step 2) at a temperature between 30 and 80° C., and recrystallizing by adding ethanol with a water-ethanol volume ratio of 4:6 or adding acetone with a water-acetone volume ratio of 5:5 while decreasing the temperature until it reaches between room temperature and −5° C., followed by centrifuging and washing the resultant crystals, to provide a thirdly purified Cefmetazole sodium after drying.

9. The process for refining Cefmetazole sodium according to claim 8, characterized in that, the organic solvent in step 1) is ethyl acetate.

10. The process for refining Cefmetazole sodium according to claim 8, characterized in that, the volume of the organic solvent in step 1) is less than one third of the volume of the aqueous solution in each extraction and the number of extractions is 2 or 3.

11. The process for refining Cefmetazole sodium according to claim 8, characterized in that, the treating temperature in step 2) is 40-80° C., and the treating time is 1-3 hours.

12. The process for refining Cefmetazole sodium according to claim 8, characterized in that, in step 3) ethanol is used to wash the crystals if recrystallizing by adding ethanol with a water-ethanol volume ratio of 4:6, and acetone is used to wash the crystals if recrystallizing by adding acetone with a water-acetone volume ratio of 5:5.

13. The process for refining Cefmetazole sodium according to claim 8, characterized in that, the temperature after adding the solvent in step 3) is cooled down to between room temperature and −5° C., and Cefmetazole sodium seed crystals are introduced optionally during the cooling process.

14. The process for refining Cefmetazole sodium according to claim 8, characterized in that, crystallization is completed between 5 and 48 hours in step 3) and the crystals can be dried by air or in vacuum.

\* \* \* \* \*